United States Patent [19]

Degner et al.

[11] Patent Number: 4,956,341
[45] Date of Patent: Sep. 11, 1990

[54] 3-TERT-BUTYL-40-METHOXYCYCLOHEX-YLMETHANOL, ITS PREPARATION AND ITS USE AS A SCENT

[75] Inventors: Dieter Degner, Dannstadt-Schauernheim; Walter Gramlich, Edingen-Neckarhausen; Ludwig Schuster, Limburgerhof, all of Fed. Rep. of Germany

[73] Assignee: BASF Aktiengesellschaft, Ludwigshafen, Fed. Rep. of Germany

[21] Appl. No.: 326,403

[22] Filed: Mar. 21, 1989

Related U.S. Application Data

[63] Continuation of Ser. No. 151,609, Feb. 2, 1988, abandoned.

[30] Foreign Application Priority Data

Feb. 19, 1987 [DE] Fed. Rep. of Germany ....... 3705299

[51] Int. Cl.$^5$ .............................................. A61K 7/46
[52] U.S. Cl. .................................... 512/23; 568/579; 252/174.11
[58] Field of Search ......................... 512/23; 568/579; 252/174.11

[56] References Cited

U.S. PATENT DOCUMENTS

| | | | |
|---|---|---|---|
| 2,450,877 | 10/1948 | Carpenter et al. | 568/520 |
| 2,450,878 | 10/1948 | Carpenter et al. | 568/520 |
| 3,993,604 | 11/1976 | Thomas et al. | 568/579 |
| 4,654,167 | 3/1987 | Degner et al. | 512/23 |

FOREIGN PATENT DOCUMENTS

| | | | |
|---|---|---|---|
| 0183970 | 10/1985 | European Pat. Off. | 512/22 |
| 2824976 | 12/1978 | Fed. Rep. of Germany | 512/28 |
| 1294932 | 4/1962 | France | 512/22 |

OTHER PUBLICATIONS

Fragrance Chemistry, The Science of the Sense of Small, E. T. Theimes, Academic Press, 1982, pp. 433–534.

The Journal of Organic Chemistry, Band 46, 1981, American Chemical Society, Books and Journals Division, pp. 4880–4885 (especially p. 4881, left col., formula 5a and p. 4884, right col., lines 43 to 55).

EP 183,970 (BASF) claims 1,3 to 5=U.S. 4,654,167.
DE 2,824,976, claim 1=U.S. 4,241,225.

Primary Examiner—James H. Reamer
Attorney, Agent, or Firm—Oblon, Spivak, McClelland, Maier & Neustadt

[57] ABSTRACT 3-tert-butyl-4-methoxycyclohexylmethanol, its preparation and its use as a scent.

2 Claims, No Drawings

3-TERT-BUTYL-4-METHOXYCYCLOHEXYLME-THANOL, ITS PREPARATION AND ITS USE AS A SCENT

This application is a continuation of application Ser. No. 07/151,609, filed on Feb. 2, 1988, now abandoned.

The present invention relates to 3-tert-butyl-4-methoxycyclohexylmethanol of the formula I and fragrance compositions containing I.

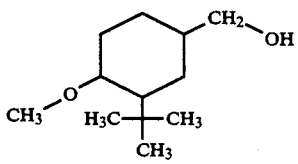

Many natural scent components are in general available in insufficient amounts, there is a necessity to adapt to changing tastes in fashion and the need for odor improvers for products in daily use, such as cleaners, cosmetics, glues, etc., is constantly increasing; the scent industry therefore constantly requires novel scents which, alone or in the form of compositions, constitute useful perfumes or fragrance materials having interesting notes. Because the relationships between structure and fragrance properties are not well known and selective synthesis of scents having the desired olfactory properties is therefore not possible, there is a need to find compounds which have useful fragrance qualities.

It is an object of the present invention to provide novel interesting scents which can be prepared in a very simple manner from readily available and therefore cheap starting materials.

We have found that this object is achieved and that the novel compound I very surprisingly possesses an extremely warm and persistent musk note.

In perfumery, compounds having a musk note have very long formed part of the most useful fragrance classes.

Whereas in earlier centuries musk fragrance was obtained virtually exclusively from the gland of the musk deer (Moschus moschiferus Linnaeus), this tincture is now virtually priceless and has since the beginning of the 20th century been steadily replaced by synthetic products (in 1888, A. Baur produced the first synthetic musk compound).

The importance of the musk fragrance is evident simply from the fact that nowadays virtually no successful perfume is composed without the use of musk compounds. The book entitled Fragrance Chemistry, The Science of the Scence of Smell, E. T. Theimer, Academic Press 1982, devotes 100 pages (433–534) to an excellent overview of the currently known, different classes of substances having the musk fragrance.

In general, musk compounds can be subdivided into three major classes:
1. Macrocyclic compounds, generally ketones, lactones or pyridines, e.g. exaltone (2), muscone (3), ambrettolide (4) or the pyridine musk (5).

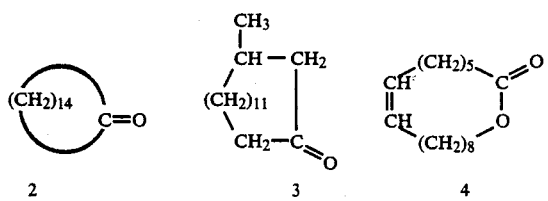

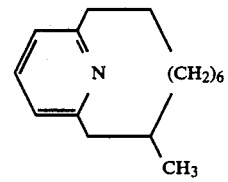

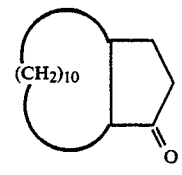

These macrocyclic compounds may also occur as bicyclic compounds, e.g. (6).

2. Aromatic mono- and bicyclic nitro compounds. Commercially important compounds are

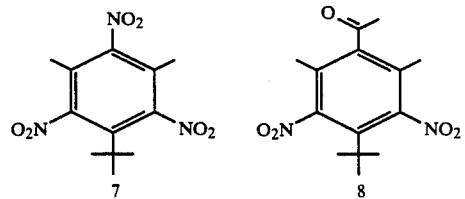

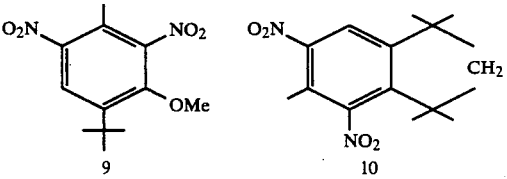

Musk xylene (7), musk ketone (8), musk ambrette (9) and moskene (10).

3. Bi- and tricyclic benzoid compounds. Commercially important bicyclic compounds are

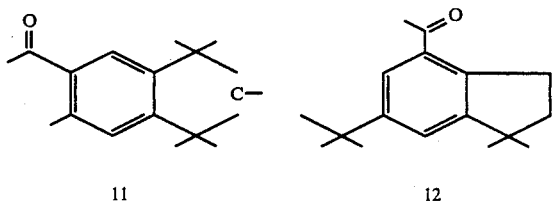

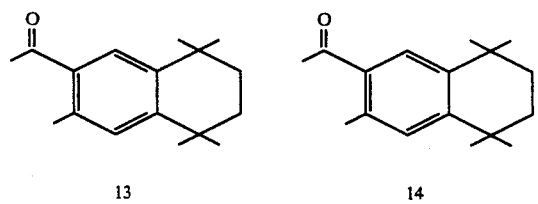

Phantolid ® (Polaks's Frutal Works; 11), Celestolide ® (JFF; 12), Versalide ® (Givaudan; 13) and tonalide (PFW; 4), and the most important tricyclic compounds are

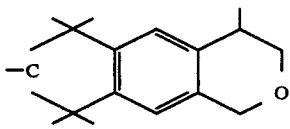

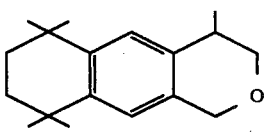

Galaxalide (15) and musk 89 (16) from JFF.

The known synthetic musk scents can generally be prepared only by expensive processes.

It was therefore completely surprising that the novel compound I, i.e. a compound which has a completely different structure and moreover can be prepared in a simple manner from readily available and therefore cheap starting materials has a warm and persistent musk fragrance.

Structurally related cyclohexylmethanols are of little commercial importance as scents, the only exception being 4-isopropylcyclohexylmethanol (17)

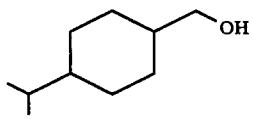

which is sold under the trade name Mayol ® (Firmenich); Mayol ® has a lily-of-the-valley fragrance, i.e. a type of fragrance which is completely different from that of the noel compound.

The compound according to the invention is prepared in a conventional manner by catalytic hydrogenation of 3-tert-butyl-4-methoxybenzaldehyde (18), which is readily obtainable from

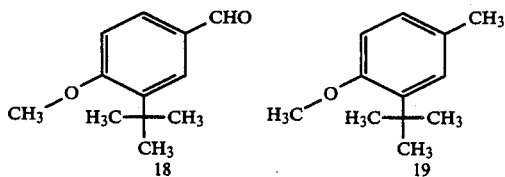

4-methyl-2-tert-butylanisole (19) by oxidation with manganese(IV) oxide by a known process (U.S. Pat. Nos. 2,450,877 and 2,450,878).

For the hydrogenation of the nucleus and the simultaneous reduction of the aldehyde group, the known nickel, palladium, rhodium or ruthenium catalysts may be used, ruthenium catalysts being preferred.

The reaction is carried out in general at from 50° to 250° C., preferably from 100° to 200° C., and under hydrogen pressures of from 30 to 500, preferably from 100 to 300, bar.

Examples of suitable solvents for the hydrogenation are alkanols, such as methanol or ethanol, ethers, such as tetrahydrofuran, hydrocarbons, such as pentane, and acids, such as acetic acid.

The product obtained in the presence of ruthenium catalysts is shown by $^1$H and $^{13}$C NMR spectroscopic investigations to be a diastereomer mixture where the isomer in which all three substituents are in the cis position predominates, i.e. contributes more than 90% (cf. Example).

The compound I obtained after purification by distillation has a warm musk fragrance which is very persistent. It is a colorless oil which is virtually insoluble in water but readily soluble in the known organic solvents.

Because of the fragrance properties described, I can advantageously be used as the scent or a component of scent compositions and perfume oils for cosmetic and industrial applications, such as household cleaners and polishes, i.e. for imparting fragrance properties to perfumes or perfumed products or improving or modifying their fragrance properties. The novel compound can be very readily combined with other scents and gives them greater persistence; moreover, it is a saturated alcohol and is therefore stable over a wide pH range, making it widely applicable. Another advantage is that, in contrast to most commercial musk scents, which are solids, the novel compound I is liquid, which ensures better processing.

EXAMPLE

Preparation of 3-tert-butyl-4-methoxycyclohexylmethanol

A mixture of 300 g (1.56 moles) of 3-tert-butyl-4-methoxybenzaldehyde, 300 ml of tetrahydrofuran and 3 g of ruthenium hydroxide [RuO(OH)$_x$] was hydrogenated in an autoclave at 150° C. and under a hydrogen pressure of 300 bar. After two hours, the hydrogenation was complete and the mixture was allowed to cool.

The catalyst was separated off and the solvent removed, after which the residue was subjected to fractional distillation under reduced pressure. After a small initial fraction, 274 g (88% yield) of a diastereomer mixture of 3-tert-butyl-4-methoxycyclohexylmethanol were obtained, in which the isomer having all three radicals in the cis position dominated with more than 90%. The product was a colorless oil having the physical properties listed below.

bp. 79° C./0.2 mbar $n_D20$ 1.4732

IR (film): 3336, 2950, 2931, 2867, 2820, 1479, 1361, 1090, 1056, 1032 cm$^{-1}$.

$^1$H NMR (CDCl$_3$): $\delta$=0.93(s,9H), 1–1.3(m,4H), 1.42–1.65(m,3H), 2.1(m,1H), 2.4(br.s,1H,-OH), 3.28(s,3H), 3.47(d,2H), 3.62(s,1H) ppm.

$^{13}$C NMR (CDCl$_3$) (Numbering scheme shown in formula):

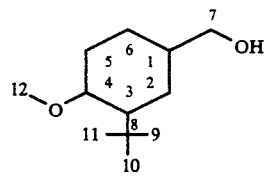

$\delta$=76.84(C$_4$,d), 68.47(C$_7$,t), 55.34(C$_{12}$,q), 50.62(C$_3$,d), 40.91(C$_1$,d), 32.67(C$_8$,s), 28.72(C$_9$,C$_{10}$,C$_{11}$;q), 27.87(C$_5$,t), 25.20(C$_6$,t), 23.20(C$_2$,t) ppm.

MS (m/I): 200 (M+,20%), 182 (5), 168 (27), 153 (7), 135 (20), 124 (48), 109 (50), 94 (88), 79 (77), 71 (100), 67 (45), 57 (90), 41 (89).

Example of use

By adding 10 parts of 3-tert-butyl-4-methoxycyclohexylmethanol to the following floral base (cf. Perfumery Technology, F. W. Wells and M. Billot, John Wiley & Sons 1981, page 276), the fragrance was rounded off with an interesting, warm musk note and given greater persistence:

| | |
|---|---|
| anisaldehyde | 40 parts by weight |
| anisyl alcohol | 5 parts by weight |
| acetophenone | 1 part by weight |
| methylacetophenone | 3 parts by weight |
| hydroxycitronellal | 8 parts by weight |
| cinnamyl alcohol | 9 parts by weight |
| citronellol | 8 parts by weight |
| heliotropine | 2 parts by weight |
| cumarin | 5 parts by weight |
| linalool | 3 parts by weight |
| 2-phenylethanol | 5 parts by weight |
| geraniol | 6 parts by weight |
| terpineol | 5 parts by weight |
| | 100 parts by weight |

We claim:
1. 3-tert-butyl-4-methoxycyclohexylmethanol.
2. A fragrance composition, comprising: 3-t-butyl-4-methoxycyclohexylmethanol in combination with the other ingredients of a cosmetic, cleanser or polish formulation.

* * * * *

UNITED STATES PATENT AND TRADEMARK OFFICE
CERTIFICATE OF CORRECTION

PATENT NO. : 4,956,341

DATED : SEPTEMBER 11, 1990

INVENTOR(S) : DIETER DEGNER ET AL.

It is certified that error appears in the above-identified patent and that said Letters Patent is hereby corrected as shown below:

ON THE TITLE PAGE:

The title of the patent is incorrect. Please delete "40" and insert --4-- after "3-TERT-BUTYL".

Signed and Sealed this

Fourteenth Day of January, 1992

Attest:

HARRY F. MANBECK, JR.

*Attesting Officer*   *Commissioner of Patents and Trademarks*